United States Patent
Bobotas (12)

(10) Patent No.: US 6,239,181 B1
(45) Date of Patent: May 29, 2001

(54) METHOD FOR PREVENTING AND TREATING PERIPHERAL NEUROPHATHY BY ADMINISTERING SELEGILINE

(75) Inventor: George Bobotas, Tarpon Springs, FL (US)

(73) Assignee: Somerset Pharmaceuticals, Inc., Tampa, FL (US)

( * ) Notice: Subject to any disclaimer, the term of this patent is extended or adjusted under 35 U.S.C. 154(b) by 0 days.

(21) Appl. No.: 09/402,752

(22) PCT Filed: Mar. 13, 1997

(86) PCT No.: PCT/US97/04584

§ 371 Date: Aug. 13, 1999

§ 102(e) Date: Aug. 13, 1999

(87) PCT Pub. No.: WO97/33572

PCT Pub. Date: Sep. 18, 1997

Related U.S. Application Data

(60) Provisional application No. 60/013,520, filed on Mar. 15, 1996.

(51) Int. Cl.$^7$ .................................................. A61K 31/135
(52) U.S. Cl. ............................................................ 514/654
(58) Field of Search .............................................. 514/654

(56) References Cited

U.S. PATENT DOCUMENTS

| | | | |
|---|---|---|---|
| 4,868,218 | 9/1989 | Buyske | 514/646 |
| 5,444,095 | 8/1995 | Tatton et al. | 514/654 |

FOREIGN PATENT DOCUMENTS

| | | | |
|---|---|---|---|
| WO 92/17169 | 10/1992 | (WO) | A61K/31/135 |

OTHER PUBLICATIONS

Broun, et al., "A Phase II Trial of Vincristine in Advanced or Recurrent Endometrial Carcinoma," *Am. J. Clin. Oncol.* 16(1):18–21 (1993).

Buys, et al., "(–)–Deprenyl Rescues Retinal Ganglion Layer Cells After Optic Nerve Crush in Adult Rats," *Invest. Ophthalmol. Vis. Sci.* 35(4):1484 (1994).

Casey, et al., "Vincristine Neuropathy: Clinicial and Electrophysiological Observations," *Brain* 96:69–86 (1973).

Gelowitz, et al., "L–Deprenyl Reduces Kainic Acid–Induced Neuronal Death in the Hippocampus," *Soc. Neurosci. Abstr.* 20:246 (1994).

Goff, et al., "A Placebo–Controlled Trial of Selegiline (L–Deprenyl) in the Treatment of Tardive Dyskinesia," *Biol. Psychiatry* 33(10):700–706 (1993).

Iwasaki, et al., "The Effect of Pergolide and Deprenyl on Axotomy–Induced Cell Death in the Spinal Motor Neuron of the Rat," *Annals of Neurology* 36(2):282–283 (1994).

Iwasaki, et al., "Deprenyl Enhances Neurite Outgrowth in Cultured Rat Spinal Ventral Horn Neurons," *J. Neurol. Sci.* 125:11–13 (1994).

Macdonald, "Neurologic Complications of Chemotherapy," *Neurologic Clinics* 9(4):955–967 (1991).

Salo et al., "Deprenyl Reduces the Death of Motoneurons Caused by Axotomy," *J. Neurosci. Res.* 31:394–400 (1992).

Tatton, "Selegiline Can Mediate Neuronal Rescue Rather Than Neuronal Protection," *Movement Disorders* 8(*Supp. 1* ):S20–S30 (1993).

Tatton, et al., "Rescue of Dying Neurons: A New Action for Deprenyl in MPTP Parkinsonism," *J. Neurosci. Res.* 30:666–672 (1991).

Tatton, et al., "'Trophic–Like' Actions of (–) Deprenyl on Neurons and Astroglia," in *Recent Advances in the Treatment of Neurodegenerative Disorders and Cognitive Dysfunction* 7:238–248 (1994).

Yu, et al., "Neuroprotective Effects of Some Monoamine Oxidase–B Inhibitors Against DSP–4–Induced Noradrenaline Depletion in the Mouse Hippocampus," *J Neurochem.* 63(5):1820–1828 (1994).

International Search Report for PCT/US97/04584.

*Primary Examiner*—James H. Reamer
(74) *Attorney, Agent, or Firm*—Vinson & Elkins LLP

(57) ABSTRACT

The present invention is directed to methods for alleviating the symptoms associated with peripheral neuropathy. The neuropathy may be the result of a genetically inherited condition, systemic disease or exposure to a toxic agent. A reduction or elimination of symptoms is obtained by administering the drug selegiline. The invention is also directed to a method for treating patients with cancer by administering a chemotherapeutic agent known to have a toxic affect on peripheral nerves together with selegiline.

23 Claims, No Drawings

METHOD FOR PREVENTING AND TREATING PERIPHERAL NEUROPHATHY BY ADMINISTERING SELEGILINE

This application claim benefit to provisional Application 60/013,520 Mar. 15, 1996.

FIELD OF THE INVENTION

The present invention relates to a medical treatment for preventing or alleviating the symptoms associated with peripheral neuropathy caused by disease or exposure to a toxic agent, e.g., a chemotherapeutic cytotoxic agent. A reduction or elimination of symptoms is accomplished by administering the drug selegiline.

BACKGROUND OF THE INVENTION

Peripheral neuropathy is associated with a wide variety of causes, including genetically acquired conditions, systemic disease or exposure to toxic agents. It can manifest itself as a dysfunction of motor, sensory, sensorimotor or autonomic nerves.

Among the most important toxic agents causing peripheral neuropathy are therapeutic agents, particularly those used for the treatment of neoplastic disease. In certain cases, peripheral neuropathy is a major complication of cancer treatment and is the main factor limiting the dosage of chemotherapeutic that can be administered to a patient (Macdonald, *Neurologic Clinics* 9:955–967 (1991)). This is true for the commonly administered agents cisplatin, paclitaxel and vincristine (Broun, et al., *Am. J. Clin. Oncol.* 16:18–21 (1993); Macdonald, *Neurologic Clinics* 9:955–967 (1991); Casey, et al., *Brain* 96:69–86 (1973)). The identification of methods for preventing or alleviating dose-limiting peripheral neuropathologic side effects would allow higher, and more therapeutically effective doses of these chemotherapeutics to be administered to patients, i.e., the therapeutic efficacy of such chemotherapeutics is typically a function of dose and therefore, increasing dosage provides increased patient survival (Macdonald, *Neurologic Clinics* 9:955–967 (1991); Oxols, *Seminars in Oncology* 16, suppl. 6:22–30 (1989)).

Beyond the potential for increasing the effectiveness of cancer chemotherapy, the identification of new methods for treating peripheral neuropathy has obvious value in alleviating the suffering of patients with a wide variety of systemic diseases and genetic conditions. In many cases, progressive neuropathy in the peripheral nervous system can be debilitating or fatal.

Although selegiline has been used extensively as a treatment for Parkinson's disease, its effectiveness in the prevention or treatment of peripheral nerve dysfunction caused by toxic agents has not been previously known. The present invention is directed to methods which rely upon this surprising and unexpected discovery to reduce or eliminate symptoms associated with peripheral nerve dysfunction.

RELATED ART

Selegiline is a potent and selective irreversible inhibitor of monoamine oxidase B (MAO-B) and has been reported to have an action in protecting or rescuing neurons of the central nervous system. For example, in a rat optic nerve crush model, selegiline has been reported to increase the survival of retinal ganglion cells that are at risk of undergoing apoptosis (Buys, et al., *Invest. Opthalmol. Vis. Sci.* 35:1484 (1994)). Selegiline has also been shown to have a neuroprotective effect in a model of axotomy-induced cell death in spinal motor neurons of the rat (Iwasaki, et al., *J. Neurol. Sci.* 125:11–13 (1994)) and to enhance neurite outgrowth in a cultured spinal cord neuron (Iwasaki, et al., *Annals of Neurology* 36:282–283 (1994)). In addition, selegiline has been reported to increase the survival of CNS neurons after exposure to various chemical toxins such as $MPP^+$, kainic acid, or DSP4 (Gelowitz, et al., *Soc. Neurosci. Abstr.* 20:246 (1994); Tatton, et al., *J. Neurosci. Res.* 31:394–400 (1992); Yu, et al., *J. Neurochem.* 63:1820–1828 (1994)).

With respect to peripheral nerves, selegiline has been reported to be capable of rescuing axotomized rat facial motor neurons (Salo, et al., *J. Neurosci. Res.* 31:394–400 (1992)). A recently issued patent also suggests that it may be used in stimulating muscle reinnervation in traumatic and non-traumatic peripheral nerve damage (U.S. Pat. No. 5,444, 095).

SUMMARY OF THE INVENTION

The present invention is based upon the discovery that selegiline can be used to prevent or alleviate the symptoms associated with peripheral neuropathy. In particular, the invention provides a method for protecting a patient from, or treating a patient for, peripheral neuropathy caused by a toxic agent by administering selegiline in an amount sufficient to reduce or eliminate one or more of the symptoms associated with the neuropathy. Typically, the patient will be a human and the toxic agent will be a chemotherapeutic agent, e.g., an agent administered for the treatment of cancer. Although the method is effective for any toxic chemotherapeutic agent causing dysfunction of peripheral nerves, it is most effective for those agents with particularly severe neuropathic side effects such as cisplatin, paclitaxel, vincristine and vinblastin Any route of delivery may be used for administering the drug, but preferred routes avoid absorption of selegiline from the gastrointestinal tract. Thus, administration transdermally, buccally, or sublingually are among the preferred methods of delivery. The preferred non-oral dose of selegiline is between 0.01 mg/kg per day and 0.15 mg/kg per day, based upon the weight of the free amine. When the oral route of delivery is used, the preferred dosage range is between 0.15 mg/kg per day and 0.75 mg/kg per day based upon the weight of the free amine (typically between about 10 and 50 mg per day).

The present invention is also directed to a method for treating a patient for peripheral neuropathy caused by a genetically inherited condition or systemic disease by administering selegiline in an amount sufficient to reduce or eliminate one or more of the symptoms associated with the neuropathy. As in the case where peripheral neuropathy is due to exposure to a toxic agent, it is preferred that selegiline be administered by a route that avoids absorption of the drug from the gastrointestinal tract. Transdermal, buccal and sublingual routes of administration are among the routes preferred. Again, the dosage of selegiline for non-oral routes of administration should be between 0.01 mg/kg per day and 0.15 mg/kg per day and, when given orally, the preferred dosage range is between 0.15 mg/kg per day and 0.75 mg/kg per day.

The present invention is also directed to a method for treating a patient with cancer by: a) administering a chemotherapeutic agent known to have a toxic effect on peripheral nerves at a dose effective at slowing the progression of the patient's cancer; b) concurrently administering selegiline to the patient at a dose effective at preventing, reducing or eliminating the peripheral neuropathy associated with the chemotherapeutic agent; and c) increasing the individual or cumulative dosage of chemotherapeutic agent until peripheral neuropathy becomes unacceptably severe. Individual dosage refers to the amount of chemotherapeutic given at a single time, e.g. in a single infusion or injection, whereas, cumulative dosage is the total amount of a chemotherapeutic administered over the full course of therapy. Thus, cumulative dosage may be increased by increasing individual dosages, extending the period of therapy or both increasing individual dosages and extending the length of therapy.

The present invention provides the following:

In a method for maximizing the individual or cumulative dose of an anti-neoplastic agent used in the treatment of a patient suffering from a cancer that exhibits a dose-dependent response to said agent, the improvement that comprises the concurrent administration of a selegiline compound in an amount sufficient to permit the individual or cumulative dose of said agent to be maximized without unacceptably severe neurotoxic side effects.

As used herein "concurrent" administration of selegiline and chemotherapeutic means that the drugs are given sufficiently close in time so that their therapeutic effects overlap. The term "unacceptably severe" refers to side effects that the patient finds intolerable or which the patient's physician judges to reflect neuropathy that poses so serious a threat to the patient's health that the dosage of chemotherapeutic agent must be reduced or terminated. Typically, the patient will be a human. The preferred chemotherapeutic agents are cisplatin, paclitaxel, vincristine and vinblastine.

As with the methods discussed previously, selegiline may be administered by any route, but routes that avoid absorption across the gastrointestinal tract, e.g., transdermal, buccal and sublingual routes, are generally preferred. The non-oral dosage of selegiline administered in conjunction with chemotherapeutic agent should, preferably, be between 0.01 mg/kg per day and 0.15 mg/kg per day based upon the weight of the free amine. In general, patients administered selegiline orally should receive a dose of between 0.15 mg/kg per day and 0.75 mg/kg per day.

DETAILED DESCRIPTION OF THE INVENTION

In the following description, reference will be made to various methodologies well known to those skilled in the art of medicine and pharmacology. Such methodologies are described in standard reference works setting forth the general principles of these disciplines.

A. Definitions

Peripheral neuropathy: As used herein, the term "peripheral neuropathy" refers to abnormal function or pathological changes in nerves located outside of the brain or spinal column. The nerves may be sensory, motor, sensorimotor or autonomic and dysfunction may manifest itself in any of the various symptoms discussed herein.

Toxic agent: For the purposes of the present invention, the term "toxic agent" is defined as any substance that, through its chemical action, impairs the normal function of one or more components of the peripheral nervous system. The definition includes agents that are airborne, ingested as a contaminant of food or drugs, or taken deliberately as part of a therapeutic regime.

Selegiline: Selegiline, also known as R—(—)—N—methyl—N—(prop-2-ynyl)-2-aminophenylpropane, L—(—)deprenyl, or R—(—)—deprenyl, has the following structural formula:

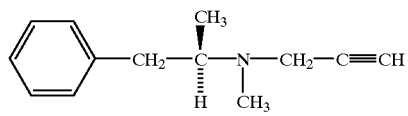

Unless otherwise specified, the term "selegiline," as used herein includes both the free base and pharmacologically acceptable salts of selegiline.

B. Symptoms of Peripheral Neuropathy

The present invention is directed to the prevention or treatment of peripheral neuropathy using selegiline. The neuropathy may be genetically acquired, developed as the result of systemic illness, or due to the exposure of a patient to a toxic agent. The treatment objective is to prevent, reduce or eliminate the symptoms associated with peripheral nerve dysfunction.

Symptoms vary widely depending upon the cause of the peripheral nerve damage and the particular types of nerves affected. Dysfunction of peripheral sensory neurons typically manifests itself as a loss of sensation in the limbs or elsewhere. For example, there may be numbness in the fingers, toes or elsewhere. Clinically, a physician may evaluate such loss by testing the ability of a patient to sense pain, vibration, or temperature or by using nerve conductance studies.

Dysfunction in peripheral motor neurons typically manifests itself as a clumsiness in performing physical tasks or as muscular weakness. For example, a patient may experience difficulty in buttoning a shirt or combing their hair. Muscular weakness may cause patients to become exhausted after relatively minor exertion and, in some cases, may create a difficulty in standing or walking. Clinically, a physician may diagnosis dysfunction in motor neurons using electrophysiological tests or by direct evaluation of patient strength or dexterity. Peripheral motor neuron dysfunction may also be diagnosed on the basis of an attenuation or absence of a neuromuscular reflex, e.g., as an absence of the ankle jerk reflex.

Dysfunction of peripheral autonomic nerves may lead a patient to experience constipation or cardiac irregularities or toxicities. It is often seen clinically as an attenuation of the postural hypotensive reflex.

C. Diseases and Toxic Agents Causing Peripheral Neuropathy

The particular systemic disease, hereditary condition or toxic agent responsible for peripheral neuropathy is not critical to the invention. Thus, selegiline is effective for neuropathies associated with systemic diseases such as: uremia; childhood cholestatic liver disease; chronic respiratory insufficiency; alcoholic polyneuropathy; multiple organ failure; sepsis; hypo-albuminemia; eosinophilia-myalgia syndrome; hepatitis; porphyria; hypo-glycemia; vitamin deficiency; chronic liver disease; primary biliary cirrhosis; hyperlipidemia; leprosy; Lyme disease; herpes zoster; Guillain-Barre syndrome; chronic inflammatory demyelinating polyradiculoneuropathy; sensory perineuritis; acquired immunodeficiency syndrome (AIDS) - associated neuropathy; Sjogren's syndrome; primary vasculitis (such as polyarteritis nodosa); allergic granulomatous angiitis; hypersensitivity angiitis; Wegener's granulomatosis; rheumatoid arthritis; systemic lupus erythematosis; mixed connective tissue disease; scleroderma; sarcoidosis; vasculitis; systemic vasculitides; acute tunnel syndrome; pandysautonomia; primary, secondary, localized or familial systemic amyloidosis; hypothyroidism; chronic obstructive pulmonary disease; acromegaly; malabsorption (sprue, celiac disease); carcinomas (sensory, sensorimotor, late and demyelinating); lymphoma (including Hodgkin's), polycythemia vera; multiple myeloma (lytic type, osteosclerotic, or solitary plasmacytoma); benign monoclonal gammopathy; macroglobulinemia; cryoglobulinemia; tropical myeloneuropathies; herpes simplex infection; cytomegalovirus infection; and diabetes.

Genetically acquired neuropathies suitable for treatment by selegiline include, without limitation: peroneal muscular atrophy (Charcot-Marie-Tooth Disease) hereditary amyloid neuropathies, hereditary sensory neuropathy (type I and type II), porphyric neuropathy, hereditary liability to pressure palsy, Fabry's Disease, adrenomyeloneuropathy, Riley-Day Syndrome, Dejerine-Sottas neuropathy (hereditary motor-sensory neuropathy-III), Refsum's disease, ataxia-telangiectasia, hereditary tyrosinemia, anaphalipoproteinemia, abetalipoproteinemia, giant axonal neuropathy, metachromatic leukodystrophy, globoid cell leukodystrophy, and Friedrich's ataxia.

A very large number of toxic agents have been described that cause peripheral neuropathy amenable to treatment by the present invention. The list includes, but is not limited to, acetazolamide, acrylamide, adriamycin, alcohol, almitrine, amiodarone, amphotericin, arsenic, aurothioglucose, carbamates, carbon disulfide, carboplatin, chloramphenicol, chloroqine, cholestyramine, cisplatin, clioquinol, colestipol, colchicine, colistin, cycloserine, cytarabine, dapsone, dideoxycytidine, dideoxyinosine, dideoxythymidine, disulfiram, doxorubicin, ethambutol, ethionamide, glutethimide, gold, hexacarbons, hormonal contraceptives, hexamethylolmelamine, hydralazine, hydroxychloroquine, imipramine, indomethacin, inorganic lead, inorganic mercury, isoniazid, lithium, methylmercury, metformin, methylbromide, methylhydrazine, metronidazole, misonidazole, nitrofurantoin, nitrogen mustard, nitrous oxide, organophosphates, ospolot, penicillin, perhexiline, perhexiline maleate, phenytoin, platinum, polychlorinated biphenyls, primidone, procarbazine, pyridoxine, sodium cyanate, streptomycin, sulphonamides, suramin, tamoxifen, paclitaxel, thalidomide, thallium, triamterene, trimethyltin, L-tryptophan, vacor, vindesine, megadoses of vitamin A, megadoses of vitamin D, and zimeldine.

Although the particular disease or toxic agent causing peripheral nerve damage is not critical, the present invention will be particularly valuable in the treatment of peripheral neuropathy resulting from the administration of chemotherapeutic agents to cancer patients. Among the chemotherapeutics known to cause peripheral neuropathy are vincristine, vinblastine, cisplatin, paclitaxel, procarbazine, dideoxyinosine, cytarabine, alpha interferon, and 5-fluorouracil (see Macdonald, *Neurologic Clinics* 9: 955–967 (1991)).

D. Method of Preventing or Treating Peripheral Neuropathy by the Administration of Selegiline Dosage The total daily dosage of selegiline administered to a patient, typically a human patient, should be at least the amount required to minimize, reduce or eliminate one or more of the symptoms associated with peripheral neuropathy, typically one of the symptoms discussed above. Ordinarily, the attending physician will administer an initial daily non-oral dose of at least about 0.01 mg per kg of body weight, calculated on the basis of the free secondary amine, with progressively higher doses being employed depending upon the response to therapy. The final daily dose will be between about 0.05 mg/kg of body weight and about 0.15 mg/kg of body weight (all such doses again being calculated on the basis of the free secondary amine).

These are simply guidelines since the actual dose must be carefully selected and titrated by the attending physician based upon clinical conditions. The optimal daily dose will be determined by methods known in the art and will be influenced by factors such as the age of the patient, the condition or disease associated with the peripheral neuropathy, the severity of both the neuropathy and the disease, the condition of the patient to whom treatment is being given, the desired degree of therapautic response, and the concomitant therapies being administered. Dosages may be provided in either a single or multiple dosage regimen Dosage Forms and Route of Administration Any route of administration and dosage form is compatible with the present invention and there are numerous references that provide guidance in this respect. For example, U.S. Pat. No. 4,812,481 discloses the use of concomitant selegiline-amantadine therapy in which selegiline is used with amantadine in oral, peroral, internal, pulmonary, rectal, nasal, vaginal, lingual, intravenous, intraarterial, intracardial, intramuscular, intraperitoneal, intracutaneous, and subcutaneous formulations. U.S. Pat. No. 5,192,550 describes a dosage form for selegiline comprising an outer wall with one or more pores, in which the wall is impermeable to selegiline but permeable to external fluids. This dosage form may have applicability for oral, sublingual, or buccal administration. Similarly, U.S. Pat. No. 5,387,615 discloses a variety of selegiline compositions, including tablets, pills, capsules, powders, aerosols, suppositories, skin patches, parenterals, and oral liquids, include oil aqueous suspensions, solutions, and emulsions. Further disclosed therein are selegiline-containing sustained release (long acting) formulations and devices.

Although any route of administration is compatible with the present invention, those that avoid the absorption of selegiline from the gastrointestinal tract are generally preferred. Thus, preferred routes include parenteral, transdermal, buccal, intraocular and sublingual administration. Parenteral compositions containing selegiline may be prepared according to conventional techniques. For example, sterile isotonic saline may be used in preparations designed for intramuscular, intravenous, intrathecal or intraarterial delivery. Sterile isotonic solutions can also be employed for intraocular administration.

Transdermal dosage unit forms can be prepared utilizing a variety of techniques that have been described in the art. For example, in U.S. Pat. Nos. 4,861,800; 4,868,218; 5,128,145; 5,190,763; and 5,242,950; and in the foreign patent documents EP-A 404807; EP-A 509761; and EP-A 593807. A monolithic patch structure can be utilized in which selegiline is directly incorporated into the adhesive and this mixture is cast on to a backing sheet. Alternatively, selegiline as an acid addition salt can be incorporated into a multi layer patch which effects a conversion of the salt to selegiline-free base, as described for example in EP-A 593807. One can also employ a device using a lyotropic liquid crystalline composition in which, for example, 5–15% of selegiline is combined with a mixture of liquid and sold polyethylene glycols, a polymer, and a non-ionic surfactant, optionally with the addition of propylene glycol and an emulsifying agent. For further details on the preparation of such transdermal formulations, reference can be made to EP-A 5509761.

Buccal and sublingual dosage forms of selegiline may be prepared utilizing techniques described in, for example, U.S.

Pat. Nos.5,192,550; 5,221,536; 5,266,332; 5,057,321; 5,446,070; 4,826,875; 5,304,379; or 5,354,885.

Form of Selegiline

The present invention is not limited to a particular form of selegiline and the drug may be used either as a free base or as a pharmaceutically acceptable acid addition salt. In the latter case, the hydrochloride salt is generally preferred. However, other salts useful in the invention include those derived from organic and inorganic acids such as, without limitation, hydrobromic acid, phosphoric acid, sulfuric acid, methane sulfonic acid, acetic acid, tartaric acid, lactic acid, succinic acid, citric acid, malic acid, maleic acid, aconitic acid, salicylic acid, thalic acid, embonic acid, enanthic acid, and the like.

Manner of Treatment

The methods disclosed herein may be used for both human and non-human subjects. With regard to the latter, the methods are particularly, but not exclusively, directed to domesticated mammals such as canine and feline species.

Treatment by the administration of selegiline should be continued until the symptoms associated with peripheral neuropathy subside. The drug may be either administered at regular intervals (e.g., twice a day) or delivered in an essentially continuous manner, e.g., via a transdermal patch. Patients should be regularly evaluated by physicians, e.g. once a week, to determine whether there has been an improvement in symptoms and whether the dosage of selegiline needs to be adjusted. Since delayed progressive neuropathy has been demonstrated after the cessation of cisplatin therapy (see e.g. Grunberg et al., *Cancer Chemother. Pharmacol.* 25:62–64 (1989)), it is preferred that administration of selegiline be continued for a period (e.g. from about 1–12 months) after the end of chemotherapy.

E. Method of Treating Cancer Patients Using a Combination of Selegiline and Chemotherapeutic The present invention is also directed to a method for treating cancer patients using a combination of chemotherapeutic agent and selegiline. Except as noted below, the same considerations discussed in the sections above apply equally to the situation in which selegiline is used as part of a therapeutic regime for such patients.

Chemotherapeutic Agents

Selegiline may be used in combination with any chemotherapeutic agent that causes peripheral neuropathy as a side effect. However, treatment is especially preferred for chemotherapeutic agents that are so toxic that their dosage is limited by the peripheral neuropathy which they cause. Included in this group are paclitaxel, cisplatin, vincristine and vinblastine. By preventing or reducing the peripheral neuropathy associated with these agents, selegiline allows higher individual doses to be administered to patients, thereby increasing the overall efficacy of the therapy. In addition, the administration of selegiline allows patients to receive a higher cumulative dose of chemotherapeutic agent. Increased cumulative dose may result from higher doses of agent being administered at each therapeutic cycle, an increase in the number of cycles, or a combination of higher doses and more cycles.

The most preferred chemotherapeutic agents for use in the present invention are cisplatin and paclitaxel, both of which have severe toxicity for peripheral nerves limiting their upper dosages (see Macdonald, *Neurologic Clinics* 9: 955–967 (1991)). Although dose intensity of these agents is an important factor in achieving optimal therapeutic results, doses substantially above about 100–120 mg/m$^2$ for cisplatin (Ozols, *Seminars in Oncology* 16: 22–30 (1989)) and about 175 mg/m$^2$ –225 mg/m$^2$ for paclitaxel (Gianni, et al., *J. Nat'l Cancer Inst.* 87:1169–75 (1995)), typically cannot be given.

The symptoms associated with peripheral neuropathy caused by the administration of cisplatin include sensory polyneuropathy with paresthesias, vibratory and proprioceptive loss, loss of pin and temperature sensation, and reduced deep tendon reflexes (see Macdonald, *Neurologic Clinics* 9:955–967 (1991); Ozols, *Seminars in Oncology* 16, suppl. 6:22–30 (1989)). Symptoms associated with other agents such as vincristine and paclitaxel include loss of deep tendon reflex response at the ankle which may progress to complete areflexia, distal symmetric sensory loss, motor weakness, foot drop, muscle atrophy, constipation, ileus, urinary retention, impotence, and postural hypotension (Id.; Casey, et al., *Brain* 96: 69–86 (1973)). For the purposes of the present invention, the severity of these symptoms is considered to be unacceptable when either a patient judges them to be intolerable or the patient's physician judges them to pose so serious a threat to the patient's health that the dosage of chemotherapeutic agent must be reduced or discontinued.

Dosage Forms and Routes of Administration

The particular route of administration that is most preferred will be determined by clinical considerations and may include any of the routes of delivery or dosage forms discussed above. Routes of administration which avoid gastrointestinal absorption will often be preferred in that these are believed to reduce the concentration of undesirable metabolic products of selegiline generated in vivo. Thus, preferred routes will typically include transdermal, parenteral, sublingual and buccal administration.

Dosage and Manner of Treatment

In some instances, patients administered selegiline according to the invention, will already have been on chemotherapy at the time that selegiline treatment is initiated. As a result, an upper limit on dosage of chemotherapeutic may already have been established, beyond which the patient experiences unacceptably severe peripheral neuropathy. In these cases, administration of the chemotherapeutic agent should be maintained and treatment with selegiline initiated at a non-oral dose of between 0.01 mg/kg of body weight per day and 0.15 mg/kg per day. The exact time at which chemotherapeutic and selegiline are given relative to one another is not critical to the invention provided that their therapeutic effects overlap. For example, it is not essential that chemotherapeutic and selegiline be administered in a single dosage form or within an hour or two of one another.

In instances in which a patient is taking multiple drugs or in which there is some reason to believe that they may be unusually sensitive to selegiline, it may be desirable to start with a low initial dose (e.g., 0.01 mg/kg) in order to ensure that the patient is able to tolerate the medication. Once this is established, the dosage may be adjusted upward with the preferred final dosage for non-oral routes of administration being approximately in the range of 0.05 to 0.15 mg/kg per day. When given orally, patients should typically receive a total daily dose of between 0.15 mg/kg per day and 0.75 mg/kg per day divided into several doses. For example, a patient may receive a dose of 5 mg orally, twice a day.

The effect of selegiline on the symptoms of peripheral neuropathy should be evaluated by the patient over a period of time and by the patient's physician on a regular basis (e.g., once a week). If the results reveal that symptoms have not subsided, the daily dosage of non-oral selegiline may be increased up to a limit of about 0.15 mg/kg. Once a concentration of selegiline is established which is effective at reducing symptoms, the dosage of chemotherapeutic is increased until a new upper limit is established, i.e. until a dosage is established which cannot be exceeded without causing unacceptable side effects. The administration of selegiline should be continued for a period of time after the administration of chemotherapeutic has ceased in order to prevent delayed progressive neuropathy. For example, the patient may continue to receive selegiline for a month or more after the end of chemotherapy.

The same basic procedure described above can be used for patients beginning chemotherapy. In these cases, both the dosage of chemotherapeutic agent and selegiline will have to be established. The preferred procedure is to begin by pretreating patients with selegiline before the administration of chemotherapeutic is begun. For example, a patient may be given 10 mg of selegiline per day for a period of one week before treatment with chemotherapeutic is initiated. The dosages of both chemotherapeutic and selegiline are then optimized as described above. Again, selegiline administration should be continued after the administration of chemotherapeutic has stopped.

The examples below are for illustrative purposes only and are not intended to limit the scope of the invention.

EXAMPLES

Example 1

Treatment of Peripheral Neuropathy Caused by Vincristine

A patient with endometrial carcinoma is given an intravenous bolus injection of vincristine at a dose of 1.4 mg/m$^2$ weekly. The toxic effects of vincristine cause sensory loss in the fingers and toes, a loss of the ankle jerk reflex, weakness and postural hypotension. The patient is administered 5 mg of selegiline hydrochloride orally twice a day, once with breakfast and once at lunch. During this time, therapy with vincristine is continued and evaluations of both tumor response and toxic side effects are carried out by a physician on a weekly basis. After continued therapy, symptoms associated with peripheral neuropathy subside. At this point, the dosage of vincristine is increased to 1.8 mg/m$^2$ and the process is continued. If symptoms of peripheral neuropathy do not return at the end of another cycle of chemotherapy, dosage is increased again until an upper limit is reached. After the final dose of vincristin is given, selegiline administration is maintained for a period of one month.

Example 2

Administration of Selegiline in Combination With Cisplatin

A patient with ovarian cancer is given weekly injections of cisplatin at a dosage of 120 mg/m$^2$. Concurrently, the patient is given an oral dose of 5 mg of selegiline hydrochloride twice a day. At the end of one week, the patient is evaluated for signs of peripheral neuropathy. If no symptoms appear, the dose of selegiline is maintained and the dosage of cisplatin is increased to 140 mg/m$^2$ per week. This process is continued until an upper limit of cisplatin is identified. The effect of the therapy on tumor progression is evaluated to determine the efficacy of the treatment.

Example 3

Treatment of Peripheral Neuropathy Caused by Paclitaxel

A patient with breast cancer is administered selegiline orally (10 mg per day) for a period of one week. At the end of this time, treatment with paclitaxel is begun by infusing the drug intravenously at a dose of 175 mg/m$^2$ over a period of 3 hours. Treatment is repeated every 3 weeks for a total of ten cycles, with the dosage of paclitaxel being increased by 25 mg/m$^2$ at each cycle. During this time, treatment with selegiline is continued and evaluations of both tumor response and toxic side effects are carried out by a physician on a weekly basis. Dosage of paclitaxel continues to be increased until side effects become unacceptably severe. Administration of selegiline is continued for one month after treatment with paclitaxel ends.

Example 4

Alternative Therapeutic Regime Using Paclitaxel and Selegiline

A patient with breast cancer is administered selegiline via a transdermal patch at a dose of about 0.10 mg/kg per day for a period of one week. At the end of this time, treatment with paclitaxel is begun by infusing the drug intravenously at a dose of 175 mg/m$^2$ over a period of 3 hours. Paclitaxel infusion is repeated every 3 weeks. During this time, treatment with selegiline is continued and evaluations of both tumor response and toxic side effects are carried out by a physician on a weekly basis. If peripheral neuropathy becomes unacceptably severe the dosage of selegiline is increased to about 0.15 mg/kg per day. If unacceptable side effects persist, the dosage of paclitaxel is reduced to 125 mg/m$^2$. Treatment cycles are continued for a period extending as long as a beneficial effect on tumor progression is obtained or until unacceptable side effects can no longer be eliminated. Administration of selegiline is continued for one month after treatment with paclitaxel ends.

All references cited herein are fully incorporated by reference. Having now fully described the invention, it will be understood by one of skill in the art that the invention may be performed within a wide and equivalent range of conditions, parameters and the like, without effecting the spirit or scope of the invention or any embodiment thereof.

What is claimed is:

1. A method of preventing or treating peripheral neuropathy caused by a chemotherapeutic agent in a patient in need of such prevention or treatment, said method comprising:
   administering selegiline to said patient in an amount sufficient to prevent, reduce or eliminate one or more of the symptoms associated with said peripheral neuropathy.

2. The method of claim 1, wherein said patient is a human.

3. The method of claim 1, wherein said agent is administered for the treatment of cancer.

4. The method of claim 3, wherein said agent is selected from the group consisting of cisplatin, paclitaxel, vincristine and vinblastin.

5. The method of claim 1, wherein said selegiline is administered by a route that avoids absorption of selegiline from the gastrointestinal tract.

6. The method of claim 5, wherein said selegiline is administered transdermally, buccally or sublingually.

7. The method of claim 5, wherein said selegiline is administered at a dose of between 0.01 mg/kg per day and 0.15 mg/kg per day based upon the weight of the free amine.

8. A method of treating a patient for peripheral neuropathy caused by a genetically inherited condition or systemic disease, said method comprising:
   administering selegiline to said patient in an amount sufficient to reduce or eliminate one or more of the symptoms associated with said peripheral neuropathy.

9. The method of claim 8, wherein said patient is a human.

10. The method of claim 8, wherein said selegiline is administered by a route that avoids absorption of selegiline from the gastrointestinal tract.

11. The method of claim 10, wherein said selegiline is administered transdermally, buccally or sublingually.

12. The method of claim 10, wherein said selegiline is administered at a dose of between 0.01 mg/kg per day and 0.15 mg/kg per day.

13. In a method for maximizing either the individual or cumulative dose of an anti-neoplastic agent used in the treatment of a patient suffering from a cancer that exhibits a dose dependent response to said agent, the improvement that comprises the concurrent administration of a selegiline compound in an amount sufficient to permit the individual or cumulative dose of said agent to be maximized without unacceptably severe neurotoxic side effects.

14. A method for treating a patient with cancer which comprises:
   a) administering to said patient a chemotherapeutic agent known to have a toxic effect on peripheral nerves, wherein said chemotherapeutic agent is administered at a dose effective at slowing the progression of said cancer;
   b) concurrently administering selegiline to said patient at a dose effective at reducing or eliminating the peripheral neuropathy associated with said chemotherapeutic agent;
   c) increasing the individual or cumulative dosage of chemotherapeutic agent until the peripheral neuropathy becomes unacceptably severe.

15. The method of claim 14, wherein said patient is a human.

16. The method of claim 14, wherein said chemotherapeutic agent is selected from the group consisting of cisplatin, paclitaxel, vincristine and vinblastin.

17. The method of claim 14, wherein said selegiline is administered by a route that avoids absorption of selegiline from the gastrointestinal tract.

18. The method of claim 17, wherein said selegiline is administered transdermally, buccally or sublingually.

19. The method of claim 17, wherein said selegiline is administered at a dose of between 0.01 mg/kg per day and 0.15 mg/kg per day.

20. The method of claim 8, wherein said peripheral neuropathy is caused by a genetically inherited condition.

21. The method of claim 8, wherein said peripheral neuropathy is caused by a systemic disease.

22. The method of claim 8, wherein said peripheral neuropathy is caused by alcoholic polyneuropathy.

23. The method of claim 8, wherein said peripheral neuropathy is caused by diabetes.

* * * * *

UNITED STATES PATENT AND TRADEMARK OFFICE
CERTIFICATE OF CORRECTION

PATENT NO. : 6,239,181 B1
DATED : May 29, 2001
INVENTOR(S) : George Bobotas

It is certified that error appears in the above-identified patent and that said Letters Patent is hereby corrected as shown below:

Title page,
In the title, please correct the word "neurophathy" to -- neuropathy --;

Claim 13,
Line 4, please insert a hyphen (-) between the words "dose" and "dependent."

Signed and Sealed this

Eighth Day of January, 2002

Attest:

JAMES E. ROGAN
*Attesting Officer*     *Director of the United States Patent and Trademark Office*

UNITED STATES PATENT AND TRADEMARK OFFICE
CERTIFICATE OF CORRECTION

PATENT NO.     : 6,239,181 B1
DATED          : May 29, 2001
INVENTOR(S)    : Bobotas It is certified that error appears in the above-identified patent and that said Letters Patent is hereby corrected as shown below:

Column 10,
Line 54, please correct the word "vinblastin" to -- vinblastine --; and Column 12,
Line 9, please correct the word "vinblastin" to -- vinblastine --.

Signed and Sealed this

Thirteenth Day of May, 2003

JAMES E. ROGAN
*Director of the United States Patent and Trademark Office*